(12) United States Patent
Zagury (10) Patent No.: US 7,641,895 B2
(45) Date of Patent: Jan. 5, 2010

(54) PEPTIDES FOR ACTIVE ANTI-CYTOKINE IMMUNIZATION

(75) Inventor: Jean-Francois Zagury, Paris (FR)

(73) Assignee: Vaxconsulting, Paris (FR)

( * ) Notice: Subject to any disclaimer, the term of this patent is extended or adjusted under 35 U.S.C. 154(b) by 0 days.

(21) Appl. No.: 12/134,743

(22) Filed: Jun. 6, 2008

(65) Prior Publication Data

US 2008/0260689 A1 Oct. 23, 2008

Related U.S. Application Data

(62) Division of application No. 10/510,116, filed as application No. PCT/FR03/001120 on Apr. 9, 2003, now Pat. No. 7,393,523.

(30) Foreign Application Priority Data

Apr. 10, 2002 (FR) .................................. 02 04463

(51) Int. Cl.
*A61K 38/19* (2006.01)
(52) U.S. Cl. ................ 424/85.1; 514/2; 514/8
(58) Field of Classification Search ........................ None
See application file for complete search history.

(56) References Cited

U.S. PATENT DOCUMENTS 6,093,405 A 7/2000 Zagury et al.
6,440,694 B1 8/2002 Bienkowski et al.

FOREIGN PATENT DOCUMENTS

| EP | 0 218 531 A2 | 4/1987 |
|---|---|---|
| WO | WO 94/01457 | 1/1994 |
| WO | WO 98/34631 A1 | 8/1998 |
| WO | WO 98/51705 A1 | 11/1998 |
| WO | WO 00/47620 A | 8/2000 |
| WO | WO 02/44197 A | 6/2002 |

OTHER PUBLICATIONS

Simon et al., Mapping of neutralizing epitopes and the receptor binding site of human interleukin1β, The Journal of Biological Chemistry, 268(13):9971-9979 (1993).
Josephson K. et al., "Noncompetitive Antibody Neutralization of IL-10 Revealed by Protein Engineering and X-Ray Crystallography", Structure, (Jul. 2002), vol. 10, No. 7, pp. 981-987.
Zagury D. et al., "Toward a new generation of vaccines: The anticytokine therapeutic vaccines", Proceedings of the National Academy of Science, (Jul. 3, 2001), vol. 98, No. 14, pp. 8024-8029.
Cha S. et al., "Crystal Structure of TRAIL-DR5 Complex Identifies a Critical Role of the Unique Frame Insertion in Conferring Recognition Specificity", Journal of Biological Chemistry, (Oct. 6, 2000), vol. 275, No. 40, pp. 31171-31177.
Bravo J., at al., "Receptor recognition by gp130 cytokines", European Molecular Biology Organization, (Jun. 1, 2000), vol. 19, No. 11, p. 2403, 2406, and 2408.
Fairbrother W.J. at al., "Novel Peptides Selected to Bind Vascular Endothelial Growth Factor Target the Receptor-Binding Site", Biochemistry American Chemical Society, (Dec. 22, 1998), pp. 17754-17764.
Chaiken I. M., et al., "Identifying structure-function relationships in four-helix bundle cytokines: towards de novo mimetics design", Trends in Biotechnology, (Oct. 1996), vol. 14, No. 10, pp. 369-375.
Capini et al., Active immunization against murine TNF-alpha peptides in mice: generation of endogenous antibodies cross-reacting with the native cytokine and in vivo protection, Vaccine, 22:3144-3153 (2004).
Firestein and Zvaifler, Anticytokine therapy in rheumatoid arthritis, The New England Journal of Medicine, 337:195-197 (Jul. 17, 1997).

*Primary Examiner*—Prema Mertz
(74) *Attorney, Agent, or Firm*—Browdy and Neimark, PLLC (57) ABSTRACT

Peptide of a size comprised between 5 and 40 amino acids, originating from a cytokine, in which at least one of its amino acids comprises at least one of its atoms separated by a distance d of less than 5 angströms from an atom of the receptor corresponding to said cytokine, the spacing d being evaluated on the basis of structural data, derivatives, immunogenic compounds comprising them, use of a peptide or peptide derivative or immunogenic compound for the preparation of a curative or preventative medicament intended for the treatment or prevention of diseases linked to an excess or to the presence of cytokines or for the treatment of an auto-immune disease and pharmaceutical compositions which contain at least one abovementioned peptide or peptide derivative or immunogenic compound as active ingredient.

4 Claims, 1 Drawing Sheet

```
                    SEQUENCE LISTING

<160> NUMBER OF SEQ ID NOS: 55

<210> SEQ ID NO 1
<211> LENGTH: 10
<212> TYPE: PRT
<213> ORGANISM: Homo sapiens

<400> SEQUENCE: 1

Ala Pro Val Ala Ser Leu Ala Cys Thr Leu
1               5                   10

<210> SEQ ID NO 2
<211> LENGTH: 11
<212> TYPE: PRT
<213> ORGANISM: Homo sapiens

<400> SEQUENCE: 2

Leu His Leu Gln Gly Gln Asp Met Glu Gln Gln
1               5                   10

<210> SEQ ID NO 3
<211> LENGTH: 10
<212> TYPE: PRT
<213> ORGANISM: Homo sapiens

<400> SEQUENCE: 3

Ser Thr Ser Gln Ala Glu Asn Met Pro Val
```

```
1               5                   10
```

<210> SEQ ID NO 4
<211> LENGTH: 16
<212> TYPE: PRT
<213> ORGANISM: Homo sapiens

<400> SEQUENCE: 4

```
Ile Met Arg Ile Lys Pro His Gln Gly Gln His Ile Gly Glu Met Ser
1               5                   10                  15
```

<210> SEQ ID NO 5
<211> LENGTH: 35
<212> TYPE: PRT
<213> ORGANISM: Homo sapiens

<400> SEQUENCE: 5

```
Pro Gln Ala Glu Gly Gln Leu Gln Trp Leu Asn Arg Arg Ala Asn Ala
1               5                   10                  15

Leu Leu Ala Asn Gly Val Glu Leu Arg Asp Asn Gln Leu Val Val Pro
            20                  25                  30

Ser Glu Gly
        35
```

<210> SEQ ID NO 6
<211> LENGTH: 16
<212> TYPE: PRT
<213> ORGANISM: Homo sapiens

<400> SEQUENCE: 6

```
Ile Ser Arg Ile Ala Val Ser Tyr Gln Thr Lys Val Asn Leu Leu Ser
1               5                   10                  15
```

<210> SEQ ID NO 7
<211> LENGTH: 15
<212> TYPE: PRT
<213> ORGANISM: Homo sapiens

<400> SEQUENCE: 7

```
Phe Gln Leu Glu Lys Gly Asp Arg Leu Ser Ala Glu Ile Asn Arg
1               5                   10                  15
```

<210> SEQ ID NO 8
<211> LENGTH: 36
<212> TYPE: PRT
<213> ORGANISM: Homo sapiens

<400> SEQUENCE: 8

```
Met Gln Asp Pro Tyr Val Lys Glu Ala Glu Asn Leu Lys Lys Tyr Phe
1               5                   10                  15

Asn Ala Gly His Ser Asp Val Ala Asp Asn Gly Thr Leu Phe Leu Gly
            20                  25                  30

Ile Leu Lys Asn
        35
```

<210> SEQ ID NO 9
<211> LENGTH: 16
<212> TYPE: PRT
<213> ORGANISM: Homo sapiens

<400> SEQUENCE: 9

```
Met Ala Glu Leu Ser Pro Ala Ala Lys Thr Gly Lys Arg Lys Arg Ser
1               5                   10                  15
```

<210> SEQ ID NO 10
<211> LENGTH: 31
<212> TYPE: PRT
<213> ORGANISM: Homo sapiens

<400> SEQUENCE: 10

Pro Asn Met Leu Arg Asp Leu Arg Asp Ala Phe Ser Arg Val Lys Thr
1               5                   10                  15
Phe Phe Gln Met Lys Asp Gln Leu Asp Asn Leu Leu Leu Lys Glu
                20                  25                  30

<210> SEQ ID NO 11
<211> LENGTH: 13
<212> TYPE: PRT
<213> ORGANISM: Homo sapiens

<400> SEQUENCE: 11

Ile Thr Leu Gln Glu Ile Ile Lys Thr Leu Asn Ser Leu
1               5                   10

<210> SEQ ID NO 12
<211> LENGTH: 26
<212> TYPE: PRT
<213> ORGANISM: Homo sapiens

<400> SEQUENCE: 12

Ala Gln Gln Phe His Arg His Lys Gln Leu Ile Arg Phe Leu Lys Arg
1               5                   10                  15
Leu Asp Arg Asn Leu Trp Gly Leu Ala Gly
                20                  25

<210> SEQ ID NO 13
<211> LENGTH: 31
<212> TYPE: PRT
<213> ORGANISM: Homo sapiens

<400> SEQUENCE: 13

Leu Leu Leu His Lys Lys Glu Asp Gly Ile Trp Ser Thr Asp Ile Leu
1               5                   10                  15
Lys Asp Gln Lys Glu Pro Lys Asn Lys Thr Phe Leu Arg Cys Glu
                20                  25                  30

<210> SEQ ID NO 14
<211> LENGTH: 11
<212> TYPE: PRT
<213> ORGANISM: Homo sapiens

<400> SEQUENCE: 14

Lys Ser Ser Arg Gly Ser Ser Asp Pro Gln Gly
1               5                   10

<210> SEQ ID NO 15
<211> LENGTH: 35
<212> TYPE: PRT
<213> ORGANISM: Homo sapiens

<400> SEQUENCE: 15

Tyr Phe Gly Lys Leu Glu Ser Lys Leu Ser Val Ile Arg Asn Leu Asn
1               5                   10                  15
Asp Gln Val Leu Phe Ile Asp Gln Gly Asn Arg Pro Leu Phe Glu Asp
                20                  25                  30

```
Met Thr Asp
        35

<210> SEQ ID NO 16
<211> LENGTH: 11
<212> TYPE: PRT
<213> ORGANISM: Homo sapiens

<400> SEQUENCE: 16

Cys Glu Lys Ile Ser Thr Leu Ser Cys Glu Asn
1               5                   10

<210> SEQ ID NO 17
<211> LENGTH: 17
<212> TYPE: PRT
<213> ORGANISM: Homo sapiens

<400> SEQUENCE: 17

Glu Asp Glu Leu Gly Asp Arg Ser Ile Met Phe Thr Val Gln Asn Glu
1               5                   10                  15

Asp

<210> SEQ ID NO 18
<211> LENGTH: 22
<212> TYPE: PRT
<213> ORGANISM: Homo sapiens

<400> SEQUENCE: 18

Val Glu Ile Ile Ala Thr Met Lys Lys Lys Gly Glu Lys Arg Cys Leu
1               5                   10                  15

Asn Pro Glu Ser Lys Ala
            20

<210> SEQ ID NO 19
<211> LENGTH: 26
<212> TYPE: PRT
<213> ORGANISM: Homo sapiens

<400> SEQUENCE: 19

Ile Pro Thr Ser Ala Leu Val Lys Glu Thr Leu Ala Leu Leu Ser Thr
1               5                   10                  15

His Arg Thr Leu Leu Ile Ala Asn Glu Thr
            20                  25

<210> SEQ ID NO 20
<211> LENGTH: 13
<212> TYPE: PRT
<213> ORGANISM: Homo sapiens

<400> SEQUENCE: 20

Leu Gln Glu Phe Leu Gly Val Met Asn Thr Glu Trp Ile
1               5                   10

<210> SEQ ID NO 21
<211> LENGTH: 11
<212> TYPE: PRT
<213> ORGANISM: Homo sapiens

<400> SEQUENCE: 21

Lys Arg Asp Leu Gly Trp Lys Trp Ile His Glu
1               5                   10

<210> SEQ ID NO 22
```

```
<211> LENGTH: 14
<212> TYPE: PRT
<213> ORGANISM: Homo sapiens

<400> SEQUENCE: 22

Thr Ile Leu Tyr Tyr Ile Gly Lys Thr Pro Lys Ile Glu Gln
1               5                   10

<210> SEQ ID NO 23
<211> LENGTH: 13
<212> TYPE: PRT
<213> ORGANISM: Homo sapiens

<400> SEQUENCE: 23

Ala Asn Trp Val Asn Val Ile Ser Asp Leu Lys Lys Ile
1               5                   10

<210> SEQ ID NO 24
<211> LENGTH: 36
<212> TYPE: PRT
<213> ORGANISM: Homo sapiens

<400> SEQUENCE: 24

Ser Ser Asn Gly Asn Val Thr Glu Ser Gly Cys Lys Glu Cys Glu Glu
1               5                   10                  15

Leu Glu Lys Lys Asn Ile Lys Glu Phe Leu Gln Ser Phe Val His Ile
                20                  25                  30

Val Gln Met Phe
            35

<210> SEQ ID NO 25
<211> LENGTH: 12
<212> TYPE: PRT
<213> ORGANISM: Homo sapiens

<400> SEQUENCE: 25

Lys Gln Ile Arg Tyr Ile Leu Asp Gly Ile Ser Ala
1               5                   10

<210> SEQ ID NO 26
<211> LENGTH: 36
<212> TYPE: PRT
<213> ORGANISM: Homo sapiens

<400> SEQUENCE: 26

Arg Ala Val Gln Met Ser Thr Lys Val Leu Ile Gln Phe Leu Gln Lys
1               5                   10                  15

Lys Ala Lys Asn Leu Asp Ala Ile Thr Thr Pro Asp Pro Thr Thr Asn
                20                  25                  30

Ala Ser Leu Leu
            35

<210> SEQ ID NO 27
<211> LENGTH: 19
<212> TYPE: PRT
<213> ORGANISM: Homo sapiens

<400> SEQUENCE: 27

Ala Asp Pro Ser Glu Glu Trp Val Gln Lys Tyr Val Ser Asp Leu Glu
1               5                   10                  15

Leu Ser Ala
```

<210> SEQ ID NO 28
<211> LENGTH: 18
<212> TYPE: PRT
<213> ORGANISM: Homo sapiens

<400> SEQUENCE: 28

Ala Asp Pro Ser Glu Ser Trp Val Gln Glu Tyr Val Tyr Asp Leu Glu
1               5                   10                  15

Leu Asn

<210> SEQ ID NO 29
<211> LENGTH: 10
<212> TYPE: PRT
<213> ORGANISM: Homo sapiens

<400> SEQUENCE: 29

Thr Ala Leu Arg Glu Leu Ile Glu Glu Leu
1               5                   10

<210> SEQ ID NO 30
<211> LENGTH: 26
<212> TYPE: PRT
<213> ORGANISM: Homo sapiens

<400> SEQUENCE: 30

Cys Ser Ala Ile Glu Lys Thr Gln Arg Met Leu Ser Gly Phe Cys Pro
1               5                   10                  15

His Lys Val Ser Ala Gly Gln Phe Ser Ser
            20                  25

<210> SEQ ID NO 31
<211> LENGTH: 14
<212> TYPE: PRT
<213> ORGANISM: Homo sapiens

<400> SEQUENCE: 31

Gly His Met Asp Leu Arg Glu Glu Gly Asp Glu Glu Thr Thr
1               5                   10

<210> SEQ ID NO 32
<211> LENGTH: 19
<212> TYPE: PRT
<213> ORGANISM: Homo sapiens

<400> SEQUENCE: 32

Leu Leu Pro Asp Ser Pro Val Gly Gln Leu His Ala Ser Leu Leu Gly
1               5                   10                  15

Leu Ser Gln

<210> SEQ ID NO 33
<211> LENGTH: 20
<212> TYPE: PRT
<213> ORGANISM: Homo sapiens

<400> SEQUENCE: 33

Leu Leu Arg Phe Lys Ile Leu Arg Ser Leu Gln Ala Phe Val Ala Val
1               5                   10                  15

Ala Ala Arg Val
            20

<210> SEQ ID NO 34
<211> LENGTH: 18
<212> TYPE: PRT

```
<213> ORGANISM: Homo sapiens

<400> SEQUENCE: 34

Ala Asn Pro Glu Lys Lys Trp Val Arg Glu Tyr Ile Asn Ser Leu Glu
1               5                   10                  15
Met Ser

<210> SEQ ID NO 35
<211> LENGTH: 12
<212> TYPE: PRT
<213> ORGANISM: Homo sapiens

<400> SEQUENCE: 35

Arg Arg Thr Leu Met Leu Leu Ala Gln Met Arg Lys
1               5                   10

<210> SEQ ID NO 36
<211> LENGTH: 27
<212> TYPE: PRT
<213> ORGANISM: Homo sapiens

<400> SEQUENCE: 36

Leu Glu Ala Cys Val Ile Gln Gly Val Gly Val Thr Glu Thr Pro Leu
1               5                   10                  15
Met Lys Glu Asp Ser Ile Leu Ala Val Arg Lys
            20                  25

<210> SEQ ID NO 37
<211> LENGTH: 12
<212> TYPE: PRT
<213> ORGANISM: Homo sapiens

<400> SEQUENCE: 37

Lys Leu His Leu Gln Gly Gln Asp Met Glu Gln Gln
1               5                   10

<210> SEQ ID NO 38
<211> LENGTH: 12
<212> TYPE: PRT
<213> ORGANISM: Homo sapiens

<400> SEQUENCE: 38

Lys Pro His Gln Gly Gln His Ile Gly Glu Met Ser
1               5                   10

<210> SEQ ID NO 39
<211> LENGTH: 30
<212> TYPE: PRT
<213> ORGANISM: Homo sapiens

<400> SEQUENCE: 39

Lys Tyr Gln Ala Glu Gly Gln Leu Gln Trp Leu Asn Arg Arg Ala Asn
1               5                   10                  15
Ala Leu Leu Ala Asn Gly Val Glu Leu Arg Asp Asn Gln Leu
            20                  25                  30

<210> SEQ ID NO 40
<211> LENGTH: 24
<212> TYPE: PRT
<213> ORGANISM: Homo sapiens

<400> SEQUENCE: 40

Lys Lys Tyr Phe Asn Ala Gly His Ser Asp Val Ala Asp Asn Gly Thr
```

```
                1               5              10              15

Leu Phe Leu Gly Ile Leu Lys Asn
                20

<210> SEQ ID NO 41
<211> LENGTH: 29
<212> TYPE: PRT
<213> ORGANISM: Homo sapiens

<400> SEQUENCE: 41

Asp Glu Cys Asn Met Leu Arg Asp Leu Arg Asp Ala Phe Ser Arg Val
1               5                   10                  15

Lys Thr Phe Phe Gln Met Lys Asp Gln Leu Asp Asn Cys
            20                  25

<210> SEQ ID NO 42
<211> LENGTH: 19
<212> TYPE: PRT
<213> ORGANISM: Homo sapiens

<400> SEQUENCE: 42

Lys Gln Leu Ile Arg Phe Leu Lys Arg Leu Asp Arg Asn Leu Trp Gly
1               5                   10                  15

Leu Ala Gly

<210> SEQ ID NO 43
<211> LENGTH: 27
<212> TYPE: PRT
<213> ORGANISM: Homo sapiens

<400> SEQUENCE: 43

Lys Lys Glu Asp Gly Ile Trp Ser Thr Asp Ile Leu Lys Asp Gln Lys
1               5                   10                  15

Glu Pro Lys Asn Lys Thr Phe Leu Arg Cys Glu
            20                  25

<210> SEQ ID NO 44
<211> LENGTH: 24
<212> TYPE: PRT
<213> ORGANISM: Homo sapiens

<400> SEQUENCE: 44

Lys Tyr Phe Gly Lys Leu Glu Ser Lys Leu Ser Val Ile Arg Asn Leu
1               5                   10                  15

Asn Asp Gln Val Leu Phe Ile Asp
            20

<210> SEQ ID NO 45
<211> LENGTH: 17
<212> TYPE: PRT
<213> ORGANISM: Homo sapiens

<400> SEQUENCE: 45

Lys Lys Lys Gly Glu Lys Arg Lys Arg Cys Leu Asn Pro Glu Ser Lys
1               5                   10                  15

Ala

<210> SEQ ID NO 46
<211> LENGTH: 14
<212> TYPE: PRT
<213> ORGANISM: Homo sapiens
```

```
<400> SEQUENCE: 46

Lys Leu Gln Glu Phe Leu Gly Val Met Asn Thr Glu Trp Ile
1               5                   10

<210> SEQ ID NO 47
<211> LENGTH: 14
<212> TYPE: PRT
<213> ORGANISM: Homo sapiens

<400> SEQUENCE: 47

Asp Thr Ile Leu Tyr Tyr Ile Gly Lys Thr Pro Lys Ile Glu
1               5                   10

<210> SEQ ID NO 48
<211> LENGTH: 30
<212> TYPE: DNA
<213> ORGANISM: Homo sapiens

<400> SEQUENCE: 48
gcacctgtac gatcactgaa ctgcacgctc                                    30

<210> SEQ ID NO 49
<211> LENGTH: 32
<212> TYPE: DNA
<213> ORGANISM: Homo sapiens

<400> SEQUENCE: 49
ctccacctcc aggacaggat atggagcaac aa                                 32

<210> SEQ ID NO 50
<211> LENGTH: 30
<212> TYPE: DNA
<213> ORGANISM: Homo sapiens

<400> SEQUENCE: 50
agcacctctc aagcagaaaa catgcccgtc                                    30

<210> SEQ ID NO 51
<211> LENGTH: 45
<212> TYPE: DNA
<213> ORGANISM: Homo sapiens

<400> SEQUENCE: 51
cagtacatca aggctaactc caagttcatc ggtatcactg agctg                   45

<210> SEQ ID NO 52
<211> LENGTH: 33
<212> TYPE: DNA
<213> ORGANISM: Homo sapiens

<400> SEQUENCE: 52
gttgacacca ccagaaaaaa tgttgactcc ctt                                33

<210> SEQ ID NO 53
<211> LENGTH: 291
<212> TYPE: DNA
<213> ORGANISM: Homo sapiens

<400> SEQUENCE: 53
gttgacacca ccagaaaaaa tgttgactcc cttggctacg gcgcacctgt acgatcactg   60
aactgcacgc tcggctacgg cgttgacacc accagaaaaa atgttgactc ccttggctac  120
ggcctccacc tccagggaca ggatatggag caacaaggct acggccagta catcaaggct  180
```

```
aactccaagt tcatcggtat cactgagctg ggctacggca gcacctctca agcagaaaac    240
atgcccgtcg gctacggcgt tgacaccacc agaaaaaatg ttgactccct t             291

<210> SEQ ID NO 54
<211> LENGTH: 9
<212> TYPE: DNA
<213> ORGANISM: Homo sapiens

<400> SEQUENCE: 54 ggctacggc                                                             9

<210> SEQ ID NO 55
<211> LENGTH: 16
<212> TYPE: PRT
<213> ORGANISM: Homo sapiens

<400> SEQUENCE: 55

Ala Gln Tyr Ile Lys Ala Asn Ser Lys Phe Ile Gly Ile Thr Glu Leu
1               5                   10                  15
```

PEPTIDES FOR ACTIVE ANTI-CYTOKINE IMMUNIZATION

CROSS-REFERENCE TO RELATED APPLICATIONS

The present application is a divisional of application Ser. No. 10/510,116, filed Jul. 19, 2005, which is the national stage under 35 U.S.C. 371 of PCT/FR2003/001120, filed Apr. 9, 2003, which claims priority from French application 02/04464, filed Apr. 10, 2002. The entire content of parent application Ser. No. 10/510,116 is herein incorporated by reference.

The present invention relates to new peptides and their use in therapeutics.

Active anti-cytokine immunization is an active immunotherapy strategy developed since 1990 by Zagury et al. which is based in particular on Patent Application WO 92/22577.

This idea was taken up by several scientific teams which have published in international scientific journals, active immunizations against the entire IFNα protein multimerized by treatment with glutaraldehyde (Gringeri et al., JAIDS 1999; 20:358-70), a chimeric TNFα protein consisting of coupling the native TNFα protein with a T epitope of ovalbumin (Dalum et al., Nature Biotechnology, 1999; 17:666-69), against entire IL9 coupled with KLH (Richard et al., PNAS, 2000; 97:767-72) or also chimeric entire IL5 with a T epitope of tetanus toxin (Hertz et al., J. Immunol, 2001; 167:3792-99).

These approaches have confirmed the feasibility of autologous anti-cytokine immunizations, but these few successes obscure the unsuccessful tests described by certain authors: certain cytokines do not allow sufficiently protective and clinically effective antibodies to be obtained, and the same cytokine prepared in a form which is effective in one manner, will not be effective in another (Richard et al., PNAS, 2000; 97:767-72).

In trying to explain this phenomenon, the Applicant has observed that to date all the authors have used entire cytokines (optionally slightly modified), which leads to difficulties in particular at the following levels:
dilution of the immunogenic power of the antigenic determinants of interest (for the B and T responses)
possible genesis of facilitating antibodies in vivo (B response).

It would therefore be desirable to have antigens available which make it possible to obtain antibodies which are sufficiently protective vis-à-vis cytokines, and limiting their activity.

WO-A-98/51705 describes h RANTES, MIP1α and MIP1β peptides comprised between the second and third cysteine of these chemokines which bind the CCR5 co-receptor.

WO-A-98/34631 describes peptides originating from γ chains of cytokine receptors used in order to block the binding of the cytokine or activation of the receptor.

WO-A-94/01457 describes IFN α peptides used as substances carrying pharmaceutical compounds.

EP-A-0218531 describes IL1 peptides used for the preparation of antibodies.

This is why a subject of the present Application is peptides of a size comprised between 5 and 40 amino acids, originating from a cytokine, characterized in that at least one of its amino acids and preferably at least two of its consecutive amino acids comprise at least one of its atoms separated by a distance d of less than 5 angströms from an atom of the receptor corresponding to said cytokine, the spacing d being evaluated on the basis of structural data (for example crystallography or NMR) and preferably in that they induce antibodies interacting with said cytokine, with the exception
of the peptides comprised between the 2nd and 3rd cysteine of h RANTES, MIP 1α and MIP 1β, and
of the peptides comprised between amino acids 123 and 140 of IFN α.

Because of their length, the cytokine peptides according to the invention correspond to a limited number of cytokine epitopes, in general to one or two cytokine epitopes, and are consequently depleted of a number of other epitopes that they contain.

By "cytokine", is meant both true cytokines as well as chemo-attractive cytokines also called chemokines. Human cytokines are preferred. By "interacting" is meant that these antibodies, for example either because they recognize the native protein, as can be shown by an immunological test (ELISA, Western Blot), or because they block the binding of the cytokine to its receptor as can be shown by a biological activity test or a biochemical competition test, have a beneficial clinical effect in vivo.

Amongst the cytokines, TGF β, IL1 α, IL1 β, vEGF, TNF α, IFN α and γ, IL 4, 5, 6, 10, 12, 13, 15, 18, 23, IP10, MIP 1α and 1β, MCP1, and Rantes can for example be mentioned. Amongst the above cytokines, TGF β, IL1 β, vEGF, TNF α, IFN α and γ, IL 4, 5, 6, 10, 12, 13, 15, 23 are preferred, or any combination of certain of these cytokines and quite particularly IL1 β, vEGF, TNF α, IL23 and IFN α or any combination of certain of these cytokines.

The cytokine peptides according to the invention originate or derive from a cytokine. By "originate" is meant that their amino acid sequence is identical to that of the cytokine. By "derive" is meant that their amino acid sequence is mostly identical to that of the cytokine but comprises a few differences as will be seen hereafter.

At least one amino acid of the cytokine peptides of the invention and preferably two consecutive amino acids possess(es) one of its atoms separated by less than 5 angströms from an atom of the receptor corresponding to said cytokine. It is advantageously separated by less than 4.5 angströms, in particular separated by less than 4 angströms and particularly separated by less than 3.5 angströms from an atom of the receptor corresponding to said cytokine.

In general the atom concerned of the amino acid is situated on the side chain of said amino acid.

Under preferential conditions for implementation of the invention 2, in particular 3 and preferably 4 consecutive amino acids of the cytokine peptide correspond to this same spacing criterion.

This spacing is evaluated on the basis of structural data, for example of crystallography, or also by NMR which produces results similar to the crystallographic measurements.

The above cytokine peptides advantageously comprise more than 8, in particular more than 10, particularly more than 12 and quite particularly more than 15 amino acids.

Under other preferential conditions of implementation of the invention, the above cytokine peptides comprise less than 35, advantageously less than 30, in particular less than 25 and particularly less than 20 amino acids. Generally the shortest sequences correspond to peptides containing a single group of at least two consecutive amino acids comprising at least one of their atoms separated by less than 5 angströms from an atom of the receptor corresponding to said cytokine, whereas the longest sequences correspond in general to peptides according to the invention containing two or even three groups or more of such consecutive amino acids. In fact these groups can be separated by several, for example 10 amino acids, as in the case of IL1β.

From the above cytokine peptides, one or more peptides are in particular retained, chosen from or originating from those, the names of which follow:

hIL1β (Human Interleukin 1 beta)
(SEQ ID No. 1)
1-APVRSLNCTL-10
(SEQ ID No. 2)
29-LHLQGQDMEQQ-39
(SEQ ID No. 3)
123-STSQAENMPV-132 hvEGF (Human vascular Endothelial Growth Factor)
(SEQ ID No. 4)
73-IMRIKPHQGQHIGEMS-88 hTNFα (Human Tumor Necrosis Factor alpha)
(SEQ ID No. 5)
20-PQAEGQLQWLNRRANALLANGVELRDNQLVVPSEG-54
(SEQ ID No. 6)
80-ISRIAVSYQTKVNLLS-95
(SEQ ID No. 7)
124-FQLEKGDRLSAEINR-138 hIFNγ (Human Interferon gamma)
(SEQ ID No. 8)
1-MQDPYVKEAENLKKYFNAGHSDVADNGTLFLGILKN-36
(SEQ ID No. 9)
118-MAELSPAAKTGKRKRS-133 hIL10 (Human Interleukin 10)
(SEQ ID No. 10)
20-PNMLRDLRDAFSRVKTFFQMKDQLDNLLLKE-50 hIL4 (Human Interleukin 4)
(SEQ ID No. 11)
5-ITLQEIIKTLNSL-17
(SEQ ID No. 12)
70-AQQFHRHKQLIRFLKRLDRNLWGLAG-95 hIL12p40 (Human Interleukin 12 sub-unit p40)
(SEQ ID No. 13)
80-LLLHKKEDGIWSTDILKDQKEPKNKTFLRCE-110
(SEQ ID No. 14)
135-KSSRGSSDPQG-145 hIL18 (Human Interleukin 18)
(SEQ ID No. 15)
1-YFGKLESKLSVIRNLNDQVLFIDQGNRPLFEDMTD-35
(SEQ ID No. 16)
68-CEKISTLSCEN-78
(SEQ ID No. 17)
141-EDELGDRSIMFTVQNED-157 hIP10 (Human Interferon gamma inducible protein)
(SEQ ID No. 18)
39-VEIIATMKKKGEKRCLNPESKA-60 hIL5 (Human Interleukin 5)
(SEQ ID No. 19)
1-IPTSALVKETLALLSTHRTLLIANET-26
(SEQ ID No. 20)
96-LQEFLGVMNTEWI-108 hTGFβ2
(Human Transforming Growth Factor beta type 2)
(SEQ ID No. 21)
25-KRDLGWKWIHE-35
(SEQ ID No. 22)
87-TILYYIGKTPKIEQ-100 hIL15 (Human Interleukin 15)
(SEQ ID No. 23)
1-ANWVNVISDLKKI-13
(SEQ ID No. 24)
74-SSNGNVTESGCKECEELEKKNIKEFLQSFVHIVQMF-111 hIL6 (Human Inlerleukin 6)
(SEQ ID No. 25)
28-KQIRYILDGISA-39
(SEQ ID No. 26)
114-RAVQMSTKVLIQFLQKKAKNLDAITTPDPTTNASLL-149 hMIP1α
(Human Macrophage Inflammatory Protein alpha)
(SEQ ID No. 27)
51-ADPSEEWVQKYVSDLELSA-69 hMIP1β
(Human Macrophage Inflammatory Protein beta)
(SEQ ID No. 28)
52-ADPSESWVQEYVYDLELN-69 hlL13 (Human Interteukin 13)
(SEQ ID No. 29)
8-TALRELIEEL-17
(SEQ ID No. 30)
57-CSAIEKTQRMLSGFCPHKVSAGQFSS-82 hIL23 (Human Interleukin 23)
(SEQ ID No. 31)
52 GHMDLREEGDEETT 65
(SEQ ID No. 32)
115 LLPDSPVGQLHASLLGLSQ 133
(SEQ ID No. 33)
160 LLRFKILRSLQAFVAVAARV 179 hRANTES
(Human Regulated upon Activation Normal T-cell expressed)
(SEQ ID No. 34)
51-ANPEKKWVREYINSLEMS-68 hIFNα (Human Interferon alpha)
(SEQ ID No. 35)
12-RRTLMLLAQMRK-23
(SEQ ID No. 36)
95-LEACVIQGVGVTETPLMKEDSILAVRK-121

The preceding sequences were chosen from the cytokines which participate in the development of human diseases due to their role in the inflammatory response or specific immune response.

The following peptides are quite particularly retained:

123-STSQAENMPV-132 of hIL1β

73-IMRIKPHQGQHIGEMS of hvEGF

20-PQAEGQLQWLNRRANALLANGVELRDNQLVVPSEG-54 of hTNFα

1-MQDPYVKEAENLKKYFNAGHSDVADNGTLFLGILKN-36 of hIFNγ

20-PNMLRDLRDAFSRVKTFFQMKDQLDNLLLKE-50 of hIL10

70-AQQFHRHKQLIRFLKRLDRNLWGLAG-95 of hIL4

1-YFGKLESKLSVIRNLNDQVLFIDQGNRPLFEDMTD-35 of hIL18

52 GHMDLREEGDEETT 65,

115 LLPDSPVGQLHASLLGLSQ 133
or

160 LLRFKILRSLQAFVAVAARV 119 of hIL23.

As is known by the person skilled in the art of immunology, modifications of the natural peptide chains are possible without however modifying the nature of the immunological properties of the immunogenic peptides. Derivatives of cytokine peptides can therefore also be mentioned, which are highly homologous to these natural sequences, for example having more than 50% homology, in particular more than 70% homology, and preferably more than 80% homology or even more than 90% homology with the corresponding native peptide whilst retaining the immunological properties of this epitopic site of the native peptide. Their homology zone can vary from 5 to 40 residues, for example from 8 to 40 residues, or also from 8 to 35 residues, preferably from 10 to 35 residues but also from 12 to 35 residues, notably from 12 to 30 residues, in particular from 15 to 30 residues and quite particularly from 15 to 25 residues.

The cytokine peptide derivatives can contain modified residues, on condition that the modifications do not appreciably reduce the immunogenicity, either by adding chemical radicals (methyl, acetyl etc.) or by stereochemical modification (use of D series amino acids). The cytokine peptide derivatives should, like the cytokine peptides induce antibodies interacting with cytokine.

The cytokine peptide derivatives according to the invention can comprise one or more modifications in the amino acids of which they are constituted, such as deletions, substitutions, additions, or functionalizations (such as acylation) of one or more amino acids, to the extent that these modifications remain within the framework specified above (immunological characters). For example, in general the replacement of a leucine residue by an isoleucine residue does not modify such properties; the modifications should generally concern less than 40% of the amino acids, in particular less than 30%, preferably less than 20% and quite particularly less then 10% of the amino acids of the natural peptide. It is important that the antibodies induced by the modified peptides are active vis-à-vis native cytokine.

These modifications are within the scope of a person skilled in the art, who can verify the incidence of the modifications by simple tests. The immunogenicity of such modified derivatives can be evaluated by ELISA after immunization of mice, the antigen tested by ELISA being the entire cytokine or the immunizing cytokine peptide, or by cytokine-receptor bond blocking tests. The possible modifications preferably affect less than 8 amino acids, advantageously less than 6 amino acids, in particular less than 4 amino acids, and particularly 3 amino acids or less, such as 2 or 1 single amino acid.

A subject of the invention is also a compound characterized in that it contains at least one abovementioned cytokine peptide or cytokine peptide derivative. Such a compound can comprise identical peptide/derivative repetitions, or different peptide/derivative combinations, either in linear form or in the form of a candelabra structure or couplings mixed with carrier proteins. Such a compound can also be presented in cyclized form. Thus cytokine peptides or cytokine peptide derivatives according to the invention can for example be inserted into longer sequences of amino acids providing in particular a better conformation or combined with exogenous T epitopes (whether for protein or DNA immunizations).

They can advantageously be associated in a covalent manner with carrier proteins such as for example KLH.

As was seen, the cytokine peptides according to the invention correspond in general to a small number of cytokine epitopes. When they are in particular inserted, combined or associated, the above compounds do not comprise other epitopes of said cytokine.

These cytokine peptides or cytokine derivatives can be included in any protein sequence which comprises no homology with the other epitopes of the natural cytokine. For example, they can be sites binding the receptor, to the ends of which a cysteine is simply added in order to confer a cyclic structure on the peptide. Another example is a peptide surrounded by sequences of T epitopes of the tetanus toxin. Yet another example can comprise a peptide corresponding to the sequence of the receptor binding site but where certain amino acids are replaced by their D series isomers in order to avoid their agonist effect. In fact, it can be optionally advantageous to use peptide derivatives which have no agonist activity on the receptor so that the immunogen does not interfere with the immune response.

In order to increase the immune response, these cytokine peptides or cytokine derivatives can be coupled to carrier proteins. The coupling methods and the carrier protein considered can be different according to the target peptide: they can for example be Keyhole Limpet Hemocyanin (KLH) protein and Tetanus Toxoid (TT) conjugated to the peptides by chemical methods well known to a person skilled in the art such as those of carbodiimide, glutaraldehyde or bis-diazotized benzidine coupling. The realization of these couplings can be facilitated by the addition or incorporation of amino acids into the sequence, such as for example lysines, histidines, tyrosines or cysteines. Such peptide compounds coupled to an exogenous T epitope (originating from plasmodium falciparum, KLH, etc.) whether chemically or genetically also come within the scope of the invention.

Network couplings of candelabra type or to molecules such as transferrin or ferritin can also be implemented in order to effectively stimulate the immune response.

The peptides according to the invention can in particular be produced by chemical synthesis or genetic engineering or any other suitable method. The synthesis of cyclic peptides, grafting, as needed, one or more amino acids at the end of the chain as cysteines in order to create a disulphide bridge makes it possible to recover part of the secondary structure that these peptide fragments possess in the three-dimensional structure of the protein.

The cytokine peptides, cytokine derivatives and their compounds according to the invention possess very useful pharmacological properties. They are in particular endowed with remarkable anti-cytokine properties. They are in fact immunogens and capable of generating in a subject antibodies recognizing the native cytokine. These peptides do not contain the numerous other epitopes originating from the cytokine to which they correspond.

These properties are illustrated hereafter in the experimental part. They justify the use of the peptides described above as medicaments.

The fact of being limited to these peptides close to the receptor binding site, to the exclusion of the other cytokine epitopes, in particular provides the advantage of limiting the generation of antibodies facilitating or potentializing cytokine activity. Moreover, they make it possible to increase the quality of the anticytokine immunization as the number of target antigenic determinants is limited.

This is why a subject of the invention is also medicaments characterized in that they are constituted by cytokine peptides or cytokine derivatives or compounds as defined above, i.e. cytokine peptides or cytokine derivatives or immunogenic compounds as defined above, or comprised between the 2nd and 3rd cysteine of h RANTES or comprised between amino acids 123 and 140 of IFN α, for their use in a method of therapeutic treatment of the human or animal body, as well as the use of such a cytokine peptide or cytokine derivative or immunogenic compound for the preparation of a curative or preventative medicament intended for the treatment or prevention of diseases linked to an excess or to the presence of cytokines.

The medicaments according to the present invention are used for example in both the curative and preventative treatment of the diseases linked to deregulation of the immune system involving overproduction of cytokines such as for example auto-immunes diseases (including, inter alia, multiple sclerosis, rheumatoid polyarthritis, psoriasis, auto-immune diabetes, lupus), allergy or asthma, cancers or AIDS. Thus it is clear that combating IL1β or TNFα can be useful in rheumatoid polyarthritis, combating IFNγ, IL18, IL23 or IL12 can be useful against multiple sclerosis or auto-immune diabetes, combating IL4, IL5 and IL13 can be useful against allergy or asthma, combating IL10 or vEGF can be useful against certain cancers. More generally the Th1/Th2 deregulations which govern the immune response itself and which in a standard fashion cause IL12, IL2, IL4, IL6, IL10, IL13, IFNγ, TNFα to intervene, can benefit from a readjustment of the equilibrium by active immunization. These are only a few examples, and a subject of the invention is also any treatment of the human body, based on active immunization (DNA or peptide) involving the abovementioned peptide sequences to the exclusion of the other cytokine epitopes. These sequences can be modified as indicated in the present description, and the DNA immunizations are carried out by simple translation from the genetic code.

The humoral immune response can be evaluated by ELISA tests or tests showing the inhibition of the native cytokine bond to its receptor. The cell response can be evaluated in the presence of cell proliferation tests vis-à-vis the peptide used.

The immunogenic active ingredients according to the invention can be used as follows:

A cytokine peptide or cytokine derivative or immunogenic compound according to the present invention, is administered to a patient, for example by sub-cutaneous or intramuscular route, in a sufficient quantity to be effective at a therapeutic level, to a subject needing such treatment. The dose administered can for example range from 1 to 1000 μg, in particular 10 to 500 μg, by sub-cutaneous route, once a month for three months, then periodically as a function of the induced serum antibodies count, for example every 2-6 months. In the same preparation two or more different immunogenic molecules can be administered in order to induce antibodies neutralizing all the deleterious functional sites in the case where a single immunogenic molecule does not carry all the active sites of the overproduced cytokine that are to be neutralized.

A subject of the invention is also the pharmaceutical compositions in particular the vaccines which contain at least one abovementioned cytokine peptide or cytokine derivative or immunogenic compound, as active ingredient.

As medicaments, a cytokine peptide or cytokine derivative or immunogenic compound of the invention can be incorporated into pharmaceutical compositions intended for any standard route in use in the field of vaccines, in particular by sub-cutaneous route, by intramuscular route, by intravenous route or by oral route. The administration can take place in a single dose or repeated once or more after a certain period of time.

This is why a subject of the present Application is also a curative or preventative pharmaceutical composition, characterized in that it comprises as active ingredient, one or more cytokine peptides or cytokine derivatives or compounds immunogens which are new or comprised between amino acids 123 and 140 of IFN α, as defined above.

The immunogenic agent can be conditioned alone or mixed with an excipient or mixture of pharmaceutically acceptable excipients as an adjuvant. A subject of the present Application is more particularly a vaccine containing as immunogen, an abovementioned cytokine peptide or cytokine derivative or immunogenic compound.

A subject of the present invention is also a process for preparing a composition described above, characterized in that, according to methods known per se, the active ingredient or ingredients are mixed with acceptable, in particular pharmaceutically acceptable excipients.

The administration to a patient of a cytokine peptide or cytokine derivative or immunogenic compound according to the invention corresponds to an active immunotherapy. It can also be useful to carry out passive immunotherapy, i.e. to provide a patient directly with the antibodies which he needs.

The vaccine preparations can be packaged for the intranasal route in the form of gel with carbopol as excipient, of nasal drops or spray and for the oral route in the form of gastroresistant capsules, sugar-coated tablets or gastroresistant granules.

In the case of DNA vaccine administered by systemic or mucosal route, the galenic presentation of the plasmid can be a suspension in a physiological liquid such as physiological PBS (phosphate buffered saline=PBS). The plasmids can be enclosed in biodegradable polymer (PLG, PLA, PCL) microspheres and administered in gastroresistant capsules for ingestion (oral route). The DNA can also be expressed in a bacterial, salmonella-type or viral-type, adenovirus or poxvirus living vector.

Finally, a subject of the present Application is a process for active immunization of patients characterized in that as immunogen, a cytokine peptide or cytokine derivative or immunogenic compound is used, as defined above, advantageously associated with a mineral, oily or synthetic immunity adjuvant.

The immunizations can be done in a standard fashion in particular by peptides or immunogenic compounds as conjugates preferably in the presence of an adjuvant, for example ISA 51 or Alum. The immunizations can be DNA-based (sequences homologous to the binding sites combined with exogenous T epitopes) using naked DNA or an expression vector containing an adapted promoter such as for example pCR3.1. The DNAs administered can be protected from the nucleases by the use of appropriate radicals (CpG etc.). In particular an initial DNA immunization can be followed by standard boosters using the peptide compounds.

The preferential conditions for implementation of the peptides described above also apply to the other subjects of the invention referred to above.

Figure 1:
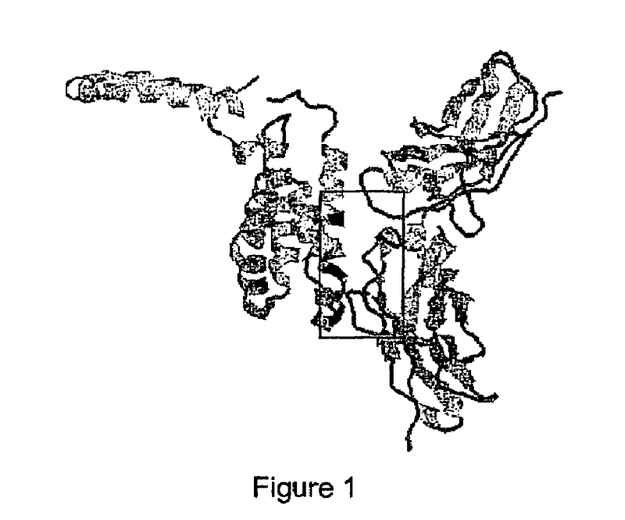
FIG. 1 schematically shows the crystallographic structure of the peptide originating from IL10 in contact with its receptor. The IL10 cytokine (on the left) can be seen in contact with its receptor (on the right).
Figure 2:
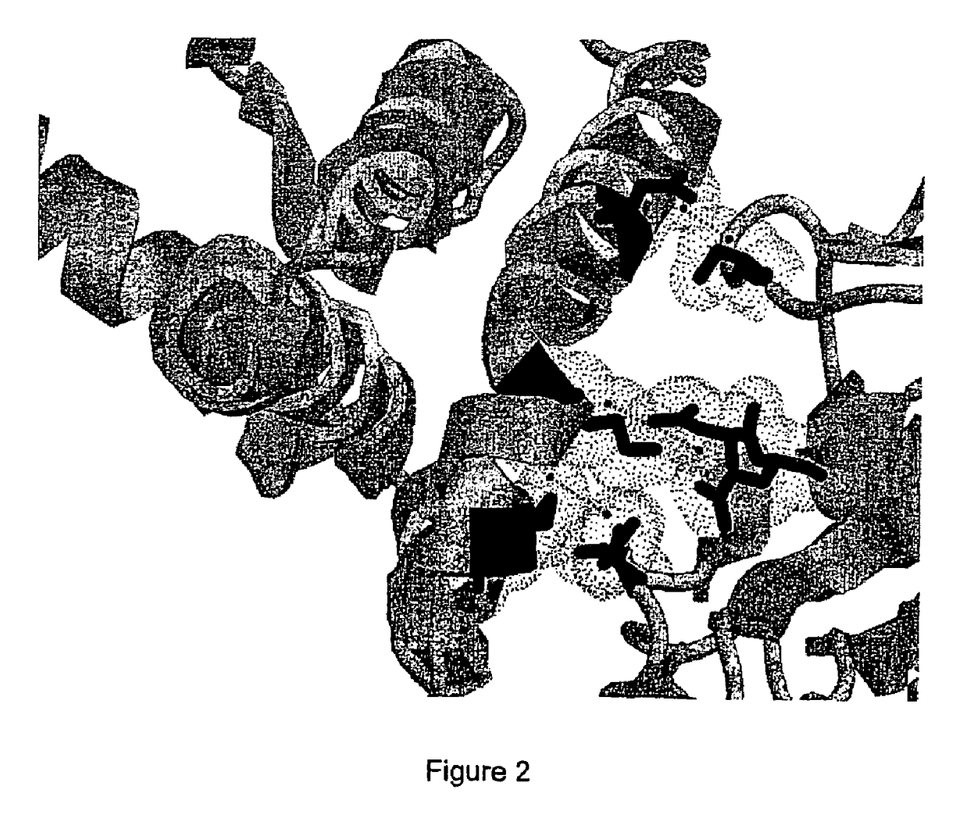
FIG. 2 is an enlargement of a portion of FIG. 1.

In FIG. 2, it can be observed that the amino acids marked in black are separated by less than 4 Angströms (d=dotted line between two black dots). They correspond, from bottom to top, to the pairs:

192IL10R serine vis-à-vis 28IL10 aspartic acid (3.18 Å), 100IL10R aspartic acid and 101IL10R glutamic acid vis-à-vis 34IL10 lysine (3.83 Å and 3.84 Å), and 94IL10R asparagine vis-à-vis 39IL10 methionine (3.70 Å). For each amino acid a central point was determined as being the baric centre of the alpha carbon of the amino acid considered, the end of the side chain and a third point chosen as being the furthest from the preceding two, on the side chain. The distance d measured is the distance separating the central points of the amino acids, respectively of the cytokine and its receptor. The distances can evidently be defined using other usual methods.

The following examples illustrate the present invention.

EXAMPLE 1

The peptide KLHLQGQDMEQQ (SEQ ID No. 37) was synthesized from the sequence of human IL1β, the K residue was added to the natural sequence in order to allow binding with KLH by coupling using glutaraldehyde. Five mice were immunized in the presence of ISA51 adjuvant. For the first injection carried out on day 0, an emulsion is prepared of 40 µg of immunogen in a quantity of ISA51 sufficient for preparing 100 µl of emulsion. For the booster on days 21 and 40, 100 µL of emulsion is prepared containing 20 µg of immunogen. Five mice were immunized in parallel as controls, with KLH in the same adjuvant.

On day 60, serum was taken and ELISA tests carried out with the native cytokine in order to reveal the presence of antibodies.

The average absorbance obtained for each mouse is presented in the table below:

| Mouse | 1 | 2 | 3 | 4 | 5 | Average |
|---|---|---|---|---|---|---|
| Peptide | 1.34 | 0.08 | 1.86 | 0.90 | 1.56 | 1.15 |
| Control | 0.05 | 0.11 | 0.08 | 0.12 | 0.06 | 0.08 |

The existence of antibodies neutralizing the native cytokine was evaluated as follows: 20 units of native IL1β cytokine are preincubated with serum from mice (immunized or control) diluted from $\frac{1}{100}^{th}$ to $\frac{1}{2000}^{th}$ over 2 hours at 37° C. The whole is then added to EL4 cells, with 50,000 cells per microwell. The production of IL2 is evaluated after 24 hours in the supernatant by a sandwich ELISA test (R&D diagnostics). The percentage inhibition of the production of IL2 indicates the percentage of neutralization of the IL1 β. As can be seen, responses are observed for the immunized mice, but not for the controls.

| Mouse | 1 | 2 | 3 | 4 | 5 | Average |
|---|---|---|---|---|---|---|
| Peptide | 52% | 25% | 93% | 86% | 8% | 52% |
| Control | 8% | −5% | 11% | 5% | 12% | 6% |

EXAMPLE 2

5 mice were immunized with the synthetic peptide originating from human vEGF: KPHQGQHIGEMS. (SEQ ID No. 38) This peptide was coupled to the carrier protein KLH by reaction with glutaraldehyde. After immunization under the same conditions as in Example 1, serum is taken on day 60 and ELISA tests are carried out with the native cytokine in order to reveal the presence of antibodies.

The average absorbance obtained for each mouse is presented in the table below:

| Mouse | 1 | 2 | 3 | 4 | 5 | Average |
|---|---|---|---|---|---|---|
| Peptide | 1.50 | 1.00 | 0.86 | 0.98 | 1.63 | 1.19 |
| Control | 0.05 | 0.13 | 0.07 | 0.10 | 0.08 | 0.09 |

EXAMPLE 3

5 mice were immunized with the synthetic peptide originating from human TNFα which is: KYQAEGQLQWLNR-RANALLANGVELRDNQL. (SEQ ID No. 39) This peptide was coupled to the carrier protein KLH by reaction with diazobenzidine. The K and Y residues were added to the natural sequence in order to allow binding with the KLH by coupling using glutaraldehyde. After immunization under the same conditions as in Example 1, serum is taken on day 60 and ELISA tests are carried out with the native cytokine in order to reveal the presence of antibodies.

The average absorbance obtained for each mouse is presented in the table below:

| Mouse | 1 | 2 | 3 | 4 | 5 | Average |
|---|---|---|---|---|---|---|
| Peptide | 1.64 | 1.14 | 1.96 | 1.02 | 0.78 | 1.31 |
| Control | 0.11 | 0.16 | 0.09 | 0.11 | 0.18 | 0.13 |

The existence of antibodies neutralizing the native cytokine was evaluated as follows: 50 units of native TNFα cytokine are preincubated with serum from mice (immunized or control) diluted $\frac{1}{200}^{th}$ over 2 hours at 37° C. The whole is then added to L929 cells, with 25,000 cells per microwell. The lysis of the cells is evaluated after 24 hours by staining with naphthol blue black (Sigma). The percentage inhibition of the lysis indicates the percentage of neutralization of the TNFα, and as can be seen, responses are observed for the immunized mice but not the controls.

| Mouse | 1 | 2 | 3 | 4 | 5 | Average |
|---|---|---|---|---|---|---|
| Peptide | 88% | 12% | 93% | 36% | 79% | 61% |
| Control | 5% | 6% | 14% | 5% | 1% | 6% |

EXAMPLE 4

5 mice were immunized with the peptide originating from human IFNγ which is: KKYFNAGHSDVAD-NGTLFLGILKN (SEQ ID No. 40). This peptide was synthetized chemically in the form of MAPS. This MAPS peptide was then coupled to the carrier protein Tetanus Toxoid by reaction with glutaraldehyde. After immunization under the same conditions as in Example 1, serum is taken on day 60 and ELISA tests are carried out with the native cytokine in order to reveal the presence of antibodies.

The average absorbance obtained for each mouse is presented in the table below:

| Mouse | 1 | 2 | 3 | 4 | 5 | Average |
|---|---|---|---|---|---|---|
| Peptide | 1.56 | 1.05 | 0.98 | 1.80 | 1.64 | 1.41 |
| Control | 0.10 | 0.12 | 0.23 | 0.08 | 0.09 | 0.12 |

The existence of antibodies neutralizing the native cytokine was evaluated as follows: 100 units of native cytokine are pre-incubated with serum from mice (immunized or control) diluted to $\frac{1}{250}^{th}$ over 2 hours at 37° C. The whole is then added to RAW 264.7 cells, with 300,000 cells being placed in 2 ml wells. The expression of class II CMH on the cells is evaluated by flux cytometry after 24 hours, by marking with class II anti-CMH antibodies coupled with fluorescein. The percentage inhibition of the expression of the class II CMH indicates the percentage of neutralization of the IFNγ, and as can be seen, inhibitions are observed for the immunized mice but not the controls. The significance threshold for these experiments is 30%.

| Mouse | 1 | 2 | 3 | 4 | 5 | Average |
|---|---|---|---|---|---|---|
| Peptide | 40% | 89% | 67% | 38% | 83% | 63% |
| Control | 25% | 14% | −10% | 29% | 7% | 13% |

EXAMPLE 5

5 mice were immunized with the peptide originating from human IL10 which is: DECNMLRDLRDAFSRVKTFFQMKDQLDNC (SEQ ID No. 41). This peptide was synthesized chemically, and a cysteine was added to each end in order to make a cyclic peptide. This peptide was then coupled with the carrier protein KLH by reaction with carbodiimide. The DE residue was also added to the natural sequence in order to allow binding with the KLH by reaction with carbodiimide. After immunization under the same conditions as in Example 1, serum is taken on day 60 and ELISA tests are carried out with the native cytokine in order to reveal the presence of antibodies.

The average absorbance obtained for each mouse is presented in the table below:

| Mouse | 1 | 2 | 3 | 4 | 5 | Average |
|---|---|---|---|---|---|---|
| Peptide | 1.94 | 0.96 | 1.85 | 0.97 | 1.5 | 1.44 |
| Control | 0.29 | 0.52 | 0.17 | 0.26 | 0.36 | 0.32 |

EXAMPLE 6

5 mice were immunized with the peptide corresponding to human IL4 which is: KQLIRFLKRLDRNLWGLAG (SEQ ID No. 42). This peptide was coupled with the carrier protein KLH by reaction with glutaraldehyde. After immunization under the same conditions as in Example 1, serum is taken on day 60 and ELISA tests are carried out with the native cytokine in order to reveal the presence of antibodies.

The average absorbance obtained for each mouse is presented in the table below:

| Mouse | 1 | 2 | 3 | 4 | 5 | Average |
|---|---|---|---|---|---|---|
| Peptide | 1.06 | 1.25 | 0.95 | 0.87 | 1.24 | 1.07 |
| Control | 0.34 | 0.09 | 0.26 | 0.16 | 0.12 | 0.19 |

EXAMPLE 7

5 mice were immunized with the peptide corresponding to human IL12p40 which is: KKEDGIWSTDILKDQKEPKNKTFLRCE (SEQ ID No. 43). This peptide was coupled with the carrier protein Tetanus Toxoid by reaction with bis-diazotized benzidine (diazo). After immunization under the same conditions as in Example 1, serum is taken on day 60 and ELISA tests are carried out with the native cytokine in order to reveal the presence of antibodies.

The average absorbance obtained for each mouse is presented in the table below:

| Mouse | 1 | 2 | 3 | 4 | 5 | Average |
|---|---|---|---|---|---|---|
| Peptide | 0.95 | 1.06 | 1.58 | 1.14 | 0.87 | 1.12 |
| Control | 0.06 | 0.12 | 0.09 | 0.05 | 0.09 | 0.08 |

EXAMPLE 8

5 mice were immunized with the peptide originating from human IL18 which is: KYFGKLESKLSVIRNLNDQVLFID (SEQ ID No. 44). This peptide was coupled with the carrier protein KLH by reaction with glutaraldehyde. The K residue was added to the natural sequence in order to allow binding with the KLH by coupling using glutaraldehyde. After immunization under the same conditions as in Example 1, serum is taken on day 60 and ELISA tests are carried out with the native cytokine in order to reveal the presence of antibodies.

The average absorbance obtained for each mouse is presented in the table below:

| Mouse | 1 | 2 | 3 | 4 | 5 | Average |
|---|---|---|---|---|---|---|
| Peptide | 1.85 | 1.13 | 0.99 | 1.24 | 1.54 | 1.35 |
| Control | 0.31 | 0.09 | 0.27 | 0.16 | 0.24 | 0.21 |

EXAMPLE 9

5 mice were immunized with the synthetic peptide originating from human IP10 which is: KKKGEKRCLNPESKA (SEQ ID No. 45). This peptide was coupled with the carrier protein Tetanus Toxoid by reaction with glutaraldehyde. The three K residues present in the natural sequence allow binding with the KLH by coupling using glutaraldehyde. After immunization under the same conditions as in Example 1, serum is taken on day 60 and ELISA tests are carried out with the native cytokine in order to reveal the presence of antibodies.

The average absorbance obtained for each mouse is presented in the table below:

| Mouse | 1 | 2 | 3 | 4 | 5 | Average |
|---|---|---|---|---|---|---|
| Peptide | 1.16 | 0.98 | 1.24 | 1.09 | 0.88 | 1.07 |
| Control | 0.32 | 0.21 | 0.11 | 0.20 | 0.09 | 0.19 |

EXAMPLE 10

5 mice were immunized with the peptide corresponding to human IL5 which is: KLQEFLGVMNTEWI (SEQ ID No. 46). This peptide was coupled with the carrier protein KLH by reaction with glutaraldehyde. The K residue was added to the natural sequence in order to allow binding with the KLH by coupling using glutaraldehyde. After immunization under the same conditions as in Example 1, serum is taken on day 60 and ELISA tests are carried out with the native cytokine in order to reveal the presence of antibodies.

The average absorbance obtained for each mouse is presented in the table below:

| Mouse | 1 | 2 | 3 | 4 | 5 | Average |
|---|---|---|---|---|---|---|
| Peptide | 1.25 | 1.21 | 1.87 | 1.10 | 0.88 | 1.26 |
| Control | 0.51 | 0.21 | 0.42 | 0.09 | 0.38 | 0.32 |

EXAMPLE 11

5 mice were immunized with the peptide corresponding to human TGFβ2 which is: DTILYYIGKTPKIE (SEQ ID No. 47). This peptide was coupled with the carrier protein KLH by reaction with carbodiimide. The D residue was added to the natural sequence in order to produce a bond by coupling. After immunization under the same conditions as in Example 1, serum is taken on day 60 and ELISA tests are carried out with the native cytokine in order to reveal the presence of antibodies.

The average absorbance obtained for each mouse is presented in the table below:

| Mouse | 1 | 2 | 3 | 4 | 5 | Average |
|---|---|---|---|---|---|---|
| Peptide | 0.95 | 1.15 | 0.99 | 1.17 | 1.08 | 1.07 |
| Control | 0.40 | 0.09 | 0.35 | 0.26 | 0.29 | 0.28 |

EXAMPLE 12

5 mice were immunized with the peptide corresponding to human IL6 which is: KQIRYILDGISA (SEQ ID No. 25). This peptide was coupled with the carrier protein TT by reaction with bis-diazotized benzidine (diazo). After immunization under the same conditions as in Example 1, serum is taken on day 60 and ELISA tests are carried out with the native cytokine in order to reveal the presence of antibodies.

The average absorbance obtained for each mouse is presented in the table below:

| Mouse | 1 | 2 | 3 | 4 | 5 | Average |
|---|---|---|---|---|---|---|
| Peptide | 1.11 | 1.27 | 1.02 | 1.34 | 0.32 | 1.01 |
| Control | 0.11 | 0.15 | 0.29 | 0.14 | 0.21 | 0.21 |

EXAMPLE 13

The DNAs corresponding to the peptides 1-APVRSLNCTL-10 (GCACCTGTACGATCACTGAACTGCACGCTC) (SEQ ID No. 48), 29-LHLQGQDMEQQ-39 (CTCCACCTCCAGGGACAGGATATGGAGCAACAA) (SEQ ID No. 49) and 123-STSQAENMPV-132 (AGCACCTCTCAAGCAGAAAACATGCCCGTC) (SEQ ID No. 50) of IL1β were synthesized and are separated from the T epitopes of the tetanus toxin:

```
                                    (SEQ ID No. 55)
AQYIKANSKFIGITEL (SEQ ID No. 51)
(CAGTACATCAAGGCTAACTCCAAGTTCATCGGTATCACTGAGCTG)

and the KLH: VDTVVRKNVDSL (SEQ ID No. 52)
(GTTGACACCACCAGAAAAAATGTTGACTCCCTT), (SEQ ID No. 54)
by GYG spacers (GGCTACGGC).
```

The final nucleotide sequence is as follows:

```
                                    (SEQ ID No. 53)
GTTGACACCACCAGAAAAAATGTTGACTCCCTTGGCTACGGCGCACCTGT
ACGATCACTGAACTGCACGCTCGGCTACGGCGTTGACACCACCAGAAAAA
ATGTTGACTCCCTTGGCTACGGCCTCCACCTCCAGGGACAGGATATGGAG
CAACAAGGCTACGGCCAGTACATCAAGGCTAACTCCAAGTTCATCGGTAT
CACTGAGCTGGGCTACGGCAGCACCTCTCAAGCAGAAAACATGCCCGTCG
GCTACGGCGTTGACACCACCAGAAAAAATGTTGACTCCCTT.
```

This DNA sequence, cloned in pRSET-A, therefore codes for a polypeptide compound that is produced and purified by genetic engineering in the form of poly-Histidine fusion protein. This polypeptide is used as immunogen as in Example 1.

The antibody response of the mice is measured against the native IL1β by ELISA and the following values are found:

| Mouse | 1 | 2 | 3 | 4 | 5 | Average |
|---|---|---|---|---|---|---|
| Peptide | 0.86 | 0.73 | 1.68 | 1.55 | 1.83 | 1.33 |
| Control | 0.23 | 0.11 | 0.21 | 0.29 | 0.17 | 0.20 |

EXAMPLE 14

The cDNAs corresponding to the peptides 1-APVRSLNCTL-10 (GCACCTGTACGATCACTGAACTGCACGCTC) (SEQ ID No. 48), 29-LHLQGQDMEQQ-39

(CTCCACCTCCAGGGACAGGATATGGAGCAACAA) (SEQ ID No. 49) and 123-STSQAENMPV-132 (AGCACCTCTCAAGCAGAAAACATGCCCGTC) (SEQ ID No. 50) of IL1β were synthesized and separated from the T epitopes of the tetanus toxin

```
                                         (SEQ ID No. 51)
AQYIKANSKFIGITEL (CAGTACATCAAGGCTAACTCCAAGTTCATCGGTATCACTGAGCTG)

and the KLH:
                                        (SEQ ID No. 52)
VDTVVRKNVDSL (GTTGACACCACCAGAAAAAATGTTGACTCCCTT)
``` by GYG spacers.

The final sequence is as follows:

```
                                        (SEQ ID No. 53)
GTTGACACCACCAGAAAAAATGTTGACTCCCTTGGCTACGGCGCACCTGT

ACGATCACTGAACTGCACGCTCGGCTACGGCGTTGACACCACCAGAAAAA

ATGTTGACTCCCTTGGCTACGGCCTCCACCTCCAGGGACAGGATATGGAG

CAACAAGGCTACGGCCAGTACATCAAGGCTAACTCCAAGTTCATCGGTAT

CACTGAGCTGGGCTACGGCAGCACCTCTCAAGCAGAAAACATGCCCGTCG

GCTACGGCGTTGACACCACCAGAAAAAATGTTGACTCCCTT.
```

This DNA sequence, cloned in pCR3.1, therefore codes for a IL1b polypeptide under the control of the CMV promoter.

A first intra-muscular injection is carried out by injecting 100 μg of vector in a saline solution of 100 μl. 2 boosters are carried out on days 21 and 40 with the peptide of Example 13 ("prime-boost" type immunization). On day 60 the antibody response is evaluated by ELISA test on the native cytokine on the 5 immunized mice and the 5 control mice.

The result is as follows:

| Mouse | 1 | 2 | 3 | 4 | 5 | Average |
|---|---|---|---|---|---|---|
| Peptide | 1.54 | 0.35 | 1.88 | 1.64 | 0.24 | 1.13 |
| Control | 0.13 | 0.11 | 0.18 | 0.08 | 0.23 | 0.14 |

EXAMPLE 15

The vaccine is formed from a water-in-oil emulsion constituted by 50% of ISA 51 (Seppic, Paris) and 50% of an aqueous solution of the peptide of Example 1 (50 μg/dose).

EXAMPLE 16

Plasmid-Immunogen-based Vaccine for DNA Vaccination of IL10 Systemic Type

Plasmids coding for the peptides APVRSLNCTL and LHLQGQDMEQQ of IL1β (20 μg/dose) were suspended in 0.2 ml of PBS for intramuscular administration.

EXAMPLE 17

A vaccine was prepared, formed from a water-in-oil emulsion constituted by 50% of ISA (SEPPIC, Paris) and 50% of an aqueous solution of the synthetic peptide KYQAEGQLQWLNRRANALLANGVELRDNQL derived from human TNFα coupled with KLH (100 μg/dose).

What is claimed is:

1. An immunizing composition, comprising a pharmaceutically acceptable excipient and, as active ingredient, an isolated peptide consisting of less than 30 amino acid residues, said peptide originating from a human cytokine, wherein said isolated peptide comprises a sequence selected from the group consisting of SEQ ID NO:2, SEQ ID NO:3, and SEQ ID NO:37.

2. The immunizing composition of claim 1, wherein said peptide comprises SEQ ID NO:2.

3. The immunizing composition of claim 1, wherein said peptide comprises SEQ ID NO:3.

4. The immunizing composition of claim 1, wherein said peptide comprises SEQ ID NO:37.

* * * * *